United States Patent [19]
Grim

[11] B 3,999,044
[45] Dec. 21, 1976

[54] INSTALLATION FOR PRODUCING RADIOLOGICAL ANGIOGRAPHIC EXPOSURES

[75] Inventor: Stig Henrik Grim, Osterskar, Sweden

[73] Assignee: Siemens Aktiengesellschaft, Berlin & Munich, Germany

[22] Filed: July 25, 1974

[21] Appl. No.: 491,650

[44] Published under the second Trial Voluntary Protest Program on March 9, 1976 as document No. B 491,650.

[30] Foreign Application Priority Data

Aug. 30, 1973 Germany .................. 2343796

[52] U.S. Cl. .................. 235/151; 250/401; 250/491
[51] Int. Cl.² .................. A61N 5/01
[58] Field of Search .................. 235/151, 61.12 N; 318/567, 568, 569; 340/172.5, 225; 250/402, 401

[56] References Cited
UNITED STATES PATENTS

| | | | |
|---|---|---|---|
| 2,488,324 | 11/1949 | Pegard | 340/225 |
| 2,715,703 | 8/1955 | Schuck | 318/569 X |
| 3,345,613 | 10/1967 | Bucholtz et al. | 340/172.5 |
| 3,569,813 | 3/1971 | Clark et al. | 318/569 |
| 3,725,652 | 4/1973 | Konvalina | 318/568 |
| 3,783,251 | 1/1974 | Pavkovich | 235/151 |

*Primary Examiner*—Eugene G. Botz
*Attorney, Agent, or Firm*—Hill, Gross, Simpson, Van Santen, Steadman, Chiara & Simpson

[57] ABSTRACT

An installation for producing radiological angiographic exposures, consisting of a particularly longitudinally displaceable patient support, at least one exposure apparatus, as well as setting means for adjusting the exposure apparatus prior to commencing a series of exposures, and a program control arrangement including program cards for the control of the installation in conformance with a currently desired dynamic exposure program during the period of a series of exposures. Each program card further includes an additional region for the recording of the static exposure program, which determines the setting of the installation preceding commencement of the exposure, and wherein the program control arrangement, moreover, is constructed for effecting the sorting of the static exposure program and the corresponding setting up of the installation.

9 Claims, 4 Drawing Figures 3,999,044

INSTALLATION FOR PRODUCING RADIOLOGICAL ANGIOGRAPHIC EXPOSURES

FIELD OF THE INVENTION

The present invention relates to an installation for producing radiological angiographic exposures, consisting of a particularly longitudinally displaceable patient support, at least one exposure apparatus, as well as setting means for adjusting the exposure apparatus prior to commencing a series of exposures, and a program control arrangement including program cards for the control of the installation in conformance with a currently desired dynamic exposure program during the period of a series of exposures.

DISCUSSION OF THE PRIOR ART

An installation of this type is known from the journal "Rontgentrahlen", Volume 19/1968. In this installation, a plurality of possible dynamic exposure programs, in effect, the instances for release of the injector, the exposure release by the film changer after completion of the exposures, and the longitudinal displacement of the patient support, are recorded on plexiglas cards. The respectively selected card, during the period of a series of exposures, moves through a program control arrangement so as to be thereby photoelectrically scanned whereby the scanning signals control the above-mentioned dynamic functions of the installation.

Before the dynamic exposure program can take place, the installation must be adjusted in conformance with an associated static program. The static program determines, for example, the selection of film changers, focuses, X-ray tubes, field of measurement for X-ray measuring chambers, the degree of film darkening, and the maximum exposure time for each image, in dependence upon the maximum number of images for each second. Notwithstanding the automatic sequence of the dynamic program, the static program must be manually set up in the known installation.

SUMMARY OF THE INVENTION

Accordingly, it is an object of the present invention to provide an installation for producing radiological angiographic exposures of the type described which is more fully automated with respect to the setting thereof.

The above object is inventively attained, in that each program card includes an additional region for the recording of the static exposure program, which determines the setting of the installation preceding commencement of the exposure, and wherein the program control arrangement, moreover, is constructed for effecting the sorting of the static exposure program and the corresponding setting up of the installation. In the inventive arrangement, insertion of the program card into a card sensor is sufficient for the fully automatic static and dynamic setting of the installation.

BRIEF DESCRIPTION OF THE DRAWINGS

Further details and advantages of the invention may now be ascertained from the following exemplary embodiment thereof, taken in conjunction with the accompanying drawings; in which.

DETAILED DESCRIPTION

Figure 1:
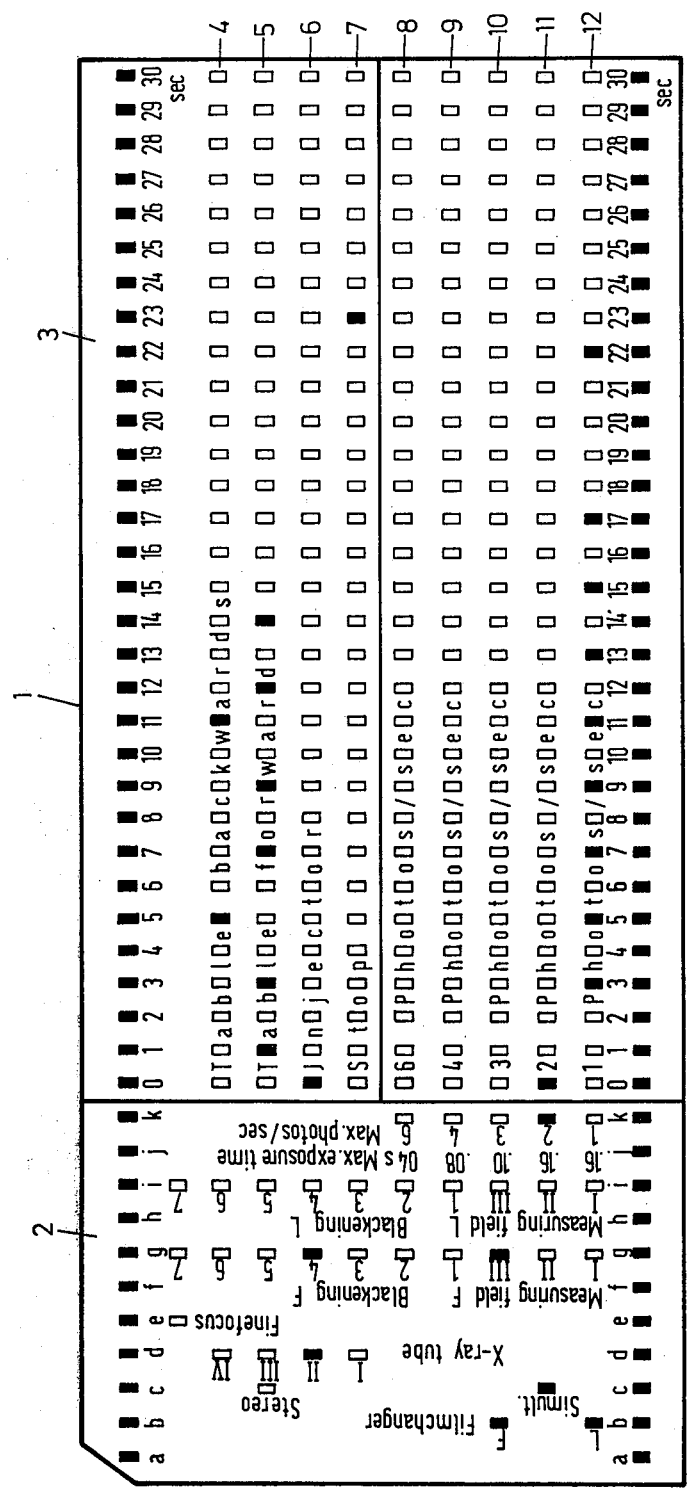
FIG. 1 illustrates a program card for use in an installation according to the present invention.

The program card 1, pursuant to FIG. 1, is formed as a punched card. The card includes a region 3 for the recording of the dynamic, and a region 2 for recording of the static exposure program. Along each longer side of the program card 1 areas are provided which, in the region 2, are identified by $a$ through $k$, and in the region 3, by 0 through 30. The distances between each of these areas correspond to respectively one second during the movement of the program card 1. The region 2 additionally includes intermediate areas $a$ through $k$ which are located between the two sides of the program card 1, a further selecting area for recording of the static exposure program which determines the adjustment of the installation preceding the commencement of the exposures.

The program card 1 is conveyed and scanned through a sensor arrangement, the latter of which is described in greater detail in connection with FIG. 2 of the drawings. The areas $a$ through $k$, and 0 through 30, serve for the control of the conveyance of the program card 1 through the sensor arrangement, while the selector areas carry out the setting up or adjustment of the installation for the exposures. The areas $a$ come first into the sensor arrangement. After 1 second, the selector areas are scanned between the areas $b$. In the illustrative example, selected and actuated are film changers L and F. The selector areas between the areas $c$ determine the selection between concurrent or alternating exposures of the film changer wherein, in this instance, a concurrent exposure is selected. The selection of the X-ray tube is carried out by means of the selector areas between the areas $d$ wherein, in the present example, the fine focus is not programmed-in between areas $e$. After 2 seconds, by means of the selector areas between the areas $g$, there is selected for the film changer F the measuring field of the X-ray measurement chamber, which is provided with three measuring areas. Concurrently carried out is the setting for the film darkening or blackening. For this purpose, there are available seven film darkening steps. After a further 2 seconds, by means of selector areas between the areas $i$, there is effected the selection of the same parameters for the film changer L. In dependence upon the number of pictures per second selected in the dynamic program region, there follows the selection of the maximum number, for example, two pictures per second, by means of the selector areas between areas $k$. The maximum exposure time at the highest picture frequency, which is dependent upon the stationary film period within the film changer, is provided between the areas $j$.

The punched lines 4 and 5 in the dynamic region 3 are provided for effecting the return and forward movement of the patient support. The line 6 controls the release of the contrast injection, and the line 7 control the switching off of the installation. The number of pictures per second is programmed by the punched lines 8 through 12.

At the moment 0, meaning in effect, when the selector areas between the areas 0 are sensed, the contrast injection is released. Concurrently, two exposures are made. After one second the patient support receives the conveying command "forward", and moves forwardly by one step. After a further 2 seconds (areas 3) there is initiated an exposure and another forward movement of the patient support. After a further 2 seconds an exposure is carried out, and a movement of the patient support backwards by one step. The further program of the program card 1 which is illustrated in FIG. 1, follows in an analogous manner.

The backward movement of the patient support is particularly suitable for peripheral angiography, when the speed of the contrast media is different in the bones, or when later phases of the circulation are to be filmed.

Figure 2:
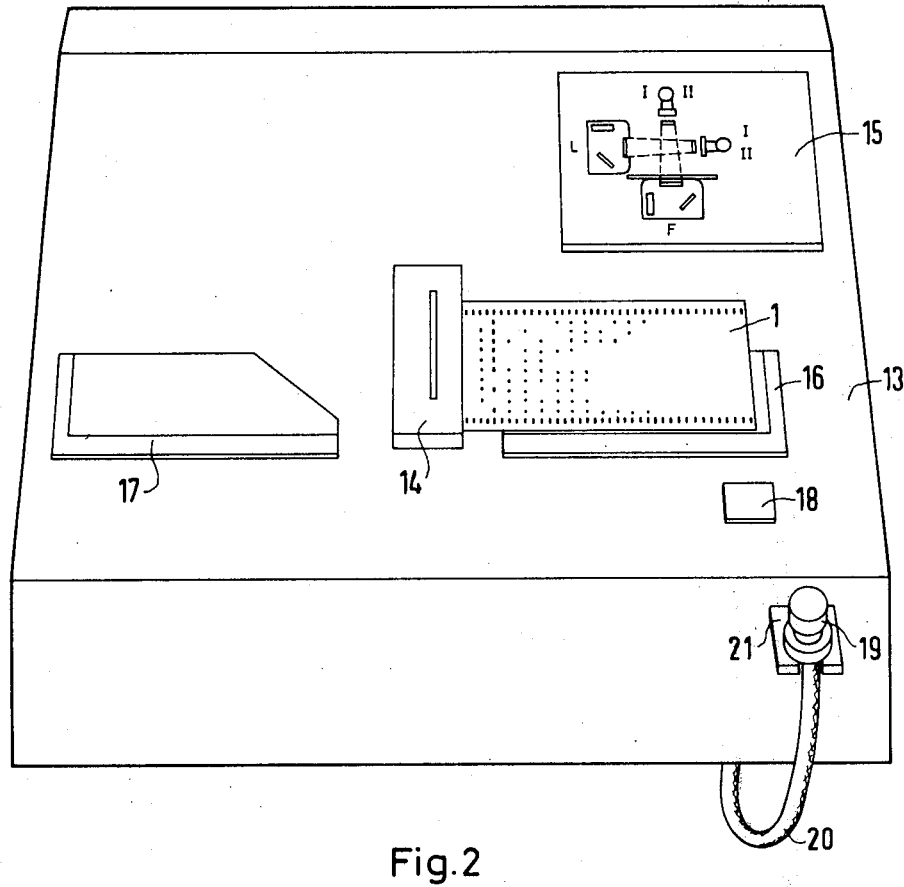
FIG. 2 shows the control panel for the installation with the card sensor.

FIG. 2 of the drawings illustrates a control panel 13 including a sensor arrangement 14, which conveys and concurrently scans the program card 1. A support 16 is provided for support of the program card in its output position. A further support 17 serves to receive the card after scanning thereof in the sensor arrangement 14. Additionally located on the control panel 13 is a picture area 15 which includes illuminable display pictures of the individual components of the installation.

Through operation of the actuating knob 18 which is located on the control panel 13, the program card 1 is conveyed through the sensor arrangement 14. First, the static region 2 is scanned. Subsequent to this reading, by means of the image area 15, a recapitulation of this program is automatically assumed, in such a manner, whereby the selected individual components of the installation are illustrated through the intermediary of a lighting installation which is positioned behind the picture area. Control may be provided as to whether the selected individual components, for example, film changers and X-ray tubes, are to be achieved in an orderly sequence prior to the completion of the dynamic program. If film magazines are missing from the film changers, or when a primary shutter is closed, a blinking light signal in the picture area 15 provides indication as to the location of the error.

After the orderly selection and setting of the individual components of the installation, through actuation of the knob 19, which is connected by means of a cable 20 with the control panel 13 and removably supported on a bracket 21 which is mounted on the panel, the dynamic region 3 of the program card 1, as described in FIG. 1, may be scanned by the sensor arrangement 14.

Figure 3:
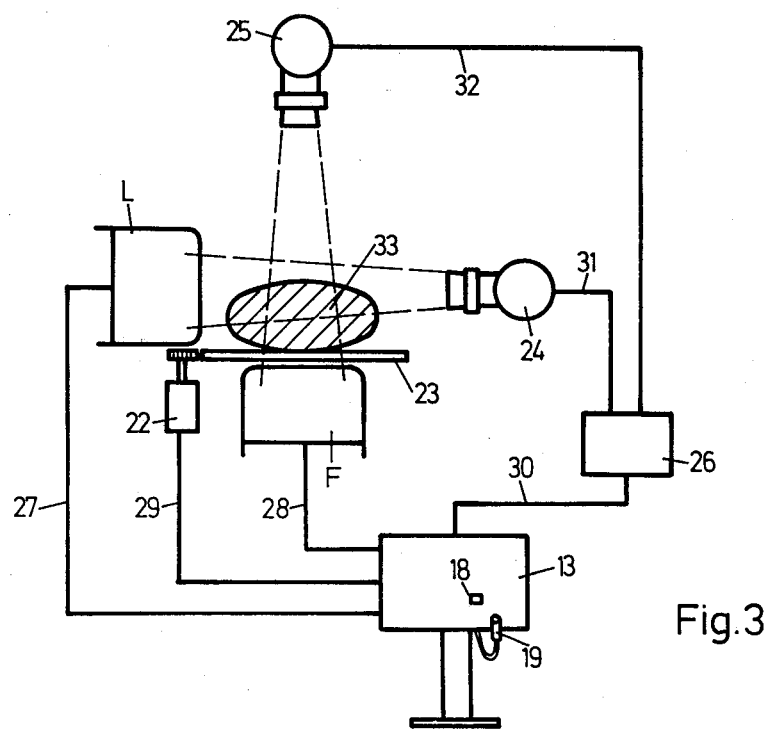
FIG. 3 schematically illustrates an installation according to the present invention.

Illustrated in FIG. 3 of the drawings is an installation for producing radiological angiographic exposures. The installation consists of a patient support 23 which longitudinally is movable through the use of a motor 22, two associated film changes L, F having, respectively, horizontally and vertically oriented film, as well as X-ray tubes 24, 25 and X-ray generator 26 for powering the X-ray tubes, and the previously mentioned control panel 13. The panel 13 is connected with the film changers L, F by means of conduits 27, 28, with the motor 22 by means of a conduit 29, and with the X-ray generator 26 through a conduit 30. The X-ray generator 26 itself is connected with the X-ray tubes 24 and 25 by means of conduits 31 and 32. The patient is herein identified by reference numeral 33. Upon actuation of knob 18, the region 2 of the program card is conveyed through and scanned by the sensor arrangement on the control panel 13. The operating parameters of the installation is so set in such a sequence during the through movement of the region 2 of the program card, as indicated and previously recorded on the card.

After the setting and control of the static exposure program the dynamic program is carried out through actuation of knob 19 on the control panel 13. In that instance, the portion 3 of the program card is conveyed through the sensor arrangement on panel 13.

Figure 4:
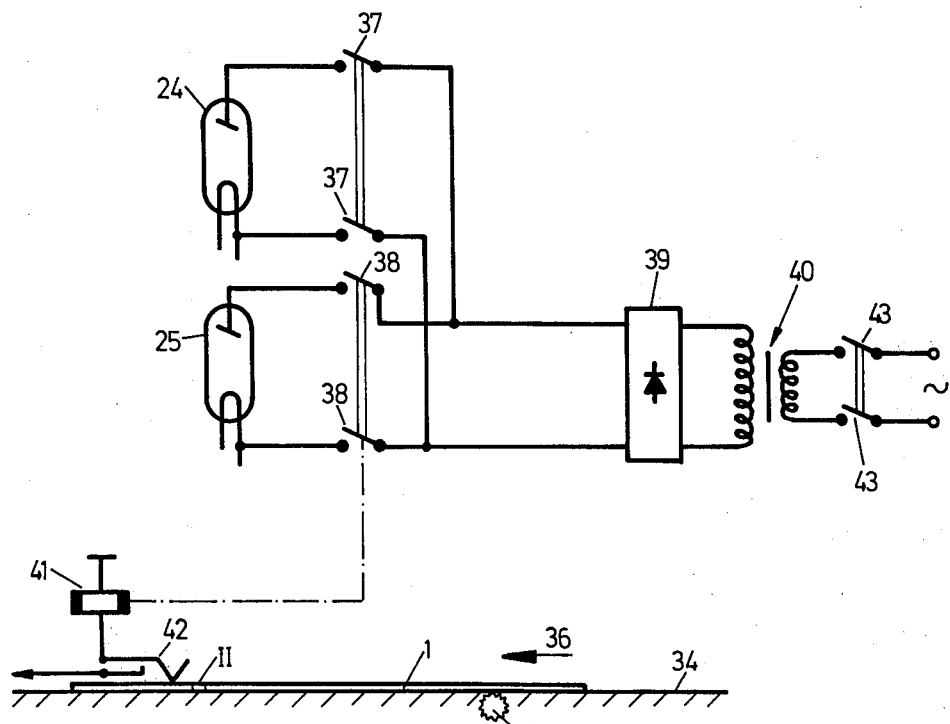
FIG. 4 shows a control circuit detail for the installation of FIG. 3.

In FIG. 4 there is elucidated, for example, the section of the respective X-ray tube preceding commencement of the exposure, meaning, within the framework of the static exposure program. FIG. 4 shows the program card 1 being supported on a stationary plate 34 on the panel 13, and which is moved along this plate, by means of a conveying arrangement 35, in the direction of arrow 36. The conveying arrangement 35, in a known manner, consists of a gear which projects upwardly through an aperture in plate 34 and upon rotation interdigitates with the areas $a$ and $k$, and $0$ through 30, of card 1.

For a closer explanation of the operation of the invention it is assumed that, pursuant to FIG. 1, the X-ray tube-representative area II is punched which is associated with the X-ray tube 25, whereby the X-ray tube 25 is to be activated. The X-ray tubes 24 and 25 are schematically illustrated in FIG. 4 of the drawings. The tubes respectively activated through contacts 37 and 38 of the output of a high-voltage rectifier 39 which is supplied by a high-voltage transformer 40. The contacts 38 are actuatable through the winding 41 of a relay which has a sensor contact 42 associated therewith and which is located on the surface of card 1, and namely along a path which traverses the punched area II.

When the area II is sensed by the contact 42, the latter is closed and the winding 41 is excited. As a result the contacts 38 are closed and the X-ray tubes 25 connected to the output of the high-voltage rectifier 39. The taking of an exposure, however, only follows when closing the switch 43 located in the primary circuit. Through the intermediary of this switch, the X-ray tube 24 may be activated upon closing of the contacts 37. These contacts 37 have a further relay winding associated therewith, by means of which a sensor may be controlled which lies on the program card 1 in a path which traverses the area I. In the same manner, the other paths across the program card 1 are scanned by feeler contacts which, through suitable relay windings, carry out the setting of the further static and dynamic data. Those contacts which serve for sensing the region II of the program card 1 are ineffective when the portion I is scanned, and conversely. The activation of the particular feeler contact is effected by means of, respectively, knobs 18 and 19.

While there has been shown what is considered to be the preferred embodiment of the invention, it will be obvious that modifications may be made which come within the scope of the disclosure of the specification.

What is claimed is:

1. In an installation for producing radiological angiographic exposures, a generally longitudinally displaceable patient support; an exposure apparatus; setting means for adjusting said exposure apparatus preceding commencement of a series of exposures; and program control means including a plurality of program cards for control of said installation during a series exposure sequence in dependence upon a particular desired dynamic exposure program, the improvement comprising; each said program card including a portion for recording a static exposure program in addition to effecting control over said installation during the dynamic exposure program so as to determine the setting of said installation preceding said exposures, said program control means including means for reading said static exposure program and for corresponding setting of said installation.

2. An installation as claimed in claim 1, said program control means including sensor means; means for conveying a preselected program card through said sensor means, said card having the portion thereof recording the static exposure program located thereon ahead of the portion recording the dynamic exposure program in the direction of conveyance through said sensor means.

3. Installation as claimed in claim 1, comprising a picture area having illuminable display pictures representative of individual components of said installation; means for illuminating said display pictures; and means for selectively controlling said illuminating means for indicating the orderly selection of said individual components preceding commencement of an exposure series.

4. Installation as claimed in claim 1, said installation including a plurality of film changers, each said program card including areas for selection of a particular film changer.

5. Installation as claimed in claim 1, said installation including a plurality of X-ray tubes, each said program card including areas for selection of a particular X-ray tube.

6. Installation as claimed in claim 1, each said program card including areas for selection of a particular X-ray focus.

7. Installation as claimed in claim 1, each said program card including areas for selection of a maximum exposure time for each X-ray picture.

8. Installation as claimed in claim 1, comprising an X-ray measurement chamber, each said program card including areas for selection of a particular measuring field for said chamber.

9. Installation as claimed in claim 8, each said program card including areas for setting the time integral of the X-ray measurement chamber flow at the termination of the exposure in correspondence with a desired degree of film darkening.

* * * * *